US007865735B2

(12) United States Patent  (10) Patent No.: US 7,865,735 B2
Yiachos  (45) Date of Patent: Jan. 4, 2011

(54) METHOD AND APPARATUS FOR MANAGING PERSONAL MEDICAL INFORMATION IN A SECURE MANNER

(76) Inventor: George Yiachos, 30 Club House Ct., Jericho, NY (US) 11753

( * ) Notice: Subject to any disclaimer, the term of this patent is extended or adjusted under 35 U.S.C. 154(b) by 1227 days.

(21) Appl. No.: 11/250,739

(22) Filed: Oct. 14, 2005

(65) Prior Publication Data

US 2006/0085347 A1  Apr. 20, 2006

Related U.S. Application Data

(60) Provisional application No. 60/620,383, filed on Oct. 19, 2004.

(51) Int. Cl.
G06F 21/00 (2006.01)
(52) U.S. Cl. .................... 713/182; 713/185
(58) Field of Classification Search ............... 713/185, 713/182
See application file for complete search history.

(56) References Cited

U.S. PATENT DOCUMENTS

| 5,832,488 | A * | 11/1998 | Eberhardt | ............... 707/10 |
| 2002/0010679 | A1 | 1/2002 | Felsher | |
| 2004/0186746 | A1 | 9/2004 | Angst et al. | |
| 2005/0197859 | A1 | 9/2005 | Wilson et al. | |
| 2005/0216313 | A1 | 9/2005 | Claud et al. | |

FOREIGN PATENT DOCUMENTS

EP  1233569  8/2002

OTHER PUBLICATIONS

"EP Search Report", *Application Serial No. 06721039.3.* (Mar. 19, 2009),53 pages.
"Foreign Office Action", *Application Serial No. 06721039.3*, (Jul. 28, 2009), 4 pages.
"Summons to Attend Oral Proceedings", *EP Application No. 06721039.3*, (Mar. 4, 2010), 5 pages.

* cited by examiner

*Primary Examiner*—Jacob Lipman

(57) ABSTRACT

A computer implemented method for managing a person's medical information includes receiving a first request to access a first tier of medical information of a given person. The request includes first security information associated with a portable secure medium associated with the given person. Access to the first tier information associated with the medical information of the given person is provided upon authenticating the first request. A second request to access a second tier of the medical information of the given person is received. The second request includes second security information provided to a medical professional or center by a medical record management center. Access to the second tier of information associated with the medical information of the given person is granted upon authenticating the second request.

28 Claims, 12 Drawing Sheets

METHOD AND APPARATUS FOR MANAGING PERSONAL MEDICAL INFORMATION IN A SECURE MANNER

CROSS-REFERENCE TO RELATED APPLICATION

The present application claims benefit of U.S. Provisional Application No. 60/620,383, filed on Oct. 19, 2004, which is incorporated by reference.

BACKGROUND

The present invention relates to managing electronic medical records. The present invention relates to the use of a secure medium in managing a user's medical records.

Providing the doctor with accurate medical records of a patient is highly important in giving the patient with the proper medical care and treatment. Sometimes, this may not be easy if the patient has visited many different doctors. Generally, each doctor keeps his or her own records. As a result, important medical information may be distributed across different doctors and may not be shared with each other. A doctor may then treat the patient without accurate medical history and records of the patient, which can harm the patient. Therefore it would be desirable to provide a method and apparatus for providing a medical professional with accurate medical records of a patient promptly.

SUMMARY

Embodiments of the present invention provide a method and apparatus for managing medical information by a user of a health information management service. Each embodiment provides one or more of the following features: (1) obtain and digitally store an enrollee's medical history; (2) collect hardcopy medical records from various physicians and institutions including handwritten notes, transcribed notes, lab results (e.g., pathologic, hematologic, radiologic, cinematic, outpatient diagnostic tests, etc.); (3) collate and digitize the material in chronological order and create a timeline/outline cover page; (4) store the accumulated medical record on a portable secure medium (e.g., credit card sized recordable CD, DVD, flash memory, etc.) and a web server (the portable secure medium is configured to behave as a security key); (5) encrypt the portable secure medium and the web server information with two levels of security; (6) create a full digitally transcribed medical record that the enrollee can carry with him or her at all times; (7) enable verified physicians to view or print any of the accessed pages on the enrollee's medical information; (8) expunge all medical information from the computer once the portable secure medium is removed from the computer; and (9) digitize each physician's records and make them available for his or her own electronic medical records system in the future.

The combined use of a login password, a portable secure medium, and a web server allows easy and secure access to the medical records by authorized personnel and at the same time being in compliance with HIPPA regulations. As used herein, "password" may refer to just the password itself or the password and login ID. The secure medium serves as a security key in accessing the medical information.

The portable secure medium is configured to be accessed by typical computers, e.g., by using computer disc drives or USB slots. When prompted, the correct username and password from the enrollee (or the patient) activates the web server to send a digital security key of first type (or decryption key) back to this client computer and give instant access to the cover page of medical information with the chronological outline of the enrollee's health history. Such information is referred to as the first tier medical information. These records are stored on the portable secure medium card/security key and/or web server as desired by the enrollee. In the present embodiment, the first tier information is stored in the portable secure medium in an encrypted form.

Access to more sensitive medical information, e.g., the "HIPPA sensitive material," is provided after a qualified physician's credentials are verified. Such information is referred to as the second tier medical information. At first the verification requires human involvement (an operator or on call person cross checking information). Subsequently, an automatic crosscheck with a database of physicians can replace this process and eliminate human involvement from the verification process. In the present implementation, a physician password is sent to the requesting physician via email/phone/fax after verification has been completed at a central office.

After receiving the password, the physician enters the password to obtain access to the second tier information. The Web server verifies the password and sends back a digital security key of second type to enable the access to the second tier information. Alternatively, the password may be emailed with a hyperlink, which leads a user to an appropriate web site when the link is clicked. The second tier information may be opened automatically upon clicking the link by automatically providing the password to the Web server. In one implementation, the second tier information is stored in the Web server and sent with the digital security key (or decryption key). In another implementation, the second tier information is stored in the portable secure medium.

The embodiments of the present invention includes one or more of the following features: (1) the proprietary software program that allows creation of the portable medical record with at least two levels of encryption, where the program enables a data entry person to click and drag/transfer prepared files, and input previously predefined passwords and gain access to the records as described above; (2) the portable, updateable records and its format, where the use of common storage media is universally readable at any institution, so that only basic computer hardware, Internet connections or phone access is required for qualified personnel to obtain instant access to medically relevant information; (3) the verification method via storage of pertinent physician credentials, time/date of request for access and purpose of access at a central website when attempts are made to access the second tier information; (4) the use of these digitally transcribed records from each physician's office for the physician's own electronic medical records; and (5) the requirement of the security key (or portable secure medium), password, and a digital security key stored in a Web server (or collectively referred to as "security triad") in combination to gain access to medical records stored on the secure medium or Web server.

The secure medium enables an unconscious patient to be identified as an enrollee to Private Health Information Systems ("PHIS"). The secure medium may be in a form of a "logo necklace" or "logo bracelet" with instructions inscribed on the reverse side on how to access the enrollee's pertinent medical records in when he or she is incapacitated. In the present embodiment, the secure medium is configured to interface with on or more types of slots (e.g., USB slots). The secure medium may work with a computer or, Personal Digital Assistants, or other types of devices with the Internet access.

In one embodiment, a portable, updateable secure medium is provided. The portable secure medium is a credit card sized portable secure medium that can be easily carried in a person's wallet or purse. The device can be smaller in other implementations. It may be incorporated into the "logo ID," e.g., in a form of a semiconductor chip. The portable secure medium includes an enrollee's medical records with at least bi-level encryption to satisfy medical and legal issues including HIPPA regulations. The portable secure medium also behaves as a security key, which when combined with a password prompts the web server to provide a digital security key that allows access to the medical records of the enrollee.

In one embodiment, a "logo ID device" identifying the patient as an enrollee to the service serves as a portable secure medium to store the medical records of the enrollee. The logo ID device is a necklace, bracelet, ring, or other types of accessories that may be worn or carried by a person. The logo ID device includes a storage device, e.g., a non-volatile semiconductor memory device. Preferably, the logo ID device has information that identifies the enrollee. The information may be the name of the enrollee or an ID number or both. The ID device may also provide or display a procedure as to how to gain access to the medical records of the enrollee, in case he or she is unconscious and cannot provide a physician with an appropriate password to access to the first tier of information.

An embodiment of the invention is directed to proprietary software used to access the medical records of the enrollee. An enrollee can decide if he or she wants his or her records stored on the secure medium or the Web server. The software allows pre-collated files to be stored on the portable secure medium or Web server with the username and password presets.

Another embodiment is directed to a method of accessing and/or managing the medical records. Access to these records, whether stored on the portable secure medium or Web server, requires three parts or security triad in the present embodiment. The first tier information is accessed when the enrollee password ("first password") is verified while the portable secure medium and the Web server are communicating through a peripheral computer. The second tier information is accessed when a physician's password ("second password") is inputted.

In one implementation, the enrollee is allowed to create his or her own portable secure medium from his or her home using the Internet. As this process becomes ubiquitous, medical records can be directly downloaded to the central office server for processing.

In another implementation, the medical records are stored in the portable secure medium itself and these records may be accessed merely by coupling the portable secure medium to a computer and entering a password. In this implementation, the medical records or information stored directly on the portable secure medium is a less sensitive information, e.g., the first tier information. More sensitive information, e.g., the second tier information, is stored in a secure server and are and transmitted to the client computer upon receiving the second password.

In one embodiment, a computer implemented method for managing a person's medical information includes receiving a first request to access a first tier of medical information of a given person, the request including first security information associated with a portable secure medium associated with the given person; providing access to the first tier information associated with the medical information of the given person upon authenticating the first request; receiving a second request to access a second tier of the medical information of the given person, the second request including second security information associated with a medical professional by a medical record management center; and providing access to the second tier information associated with the medical information of the given person upon authenticating the second request.

In another embodiment, a portable electronic secure medium for storing medical information is assigned to a given person. The secure medium comprises a non-volatile memory device; non-confidential information on the given person to whom the secure medium is assigned, and first medical information of the given person to be displayed upon first security verification, wherein the secure medium is configured to function as a security key that initiates a process to access medical records of the given person, and wherein the secure medium is configured to be coupled to a client device for communication with a remotely located server to obtain an authorization to access the medical records of the given person.

In yet another embodiment, a server for managing medical information of users includes a network interface to communicate with clients; a storage device to store medical information of the users; and a computer readable medium. The medium includes code for receiving a first request to access a first tier of medical information of a given user, the request including first security information associated with a portable secure medium associated with the given user; code for providing access to the first tier information associated with the medical information of the given user upon authenticating the first request; code for receiving a second request to access a second tier of the medical information of the given user, the second request including second security information associated with a medical professional; and code for providing access to the second tier of information associated with the medical information of the given user upon authenticating the second request.

DETAILED DESCRIPTION OF THE INVENTION

Figure 1:
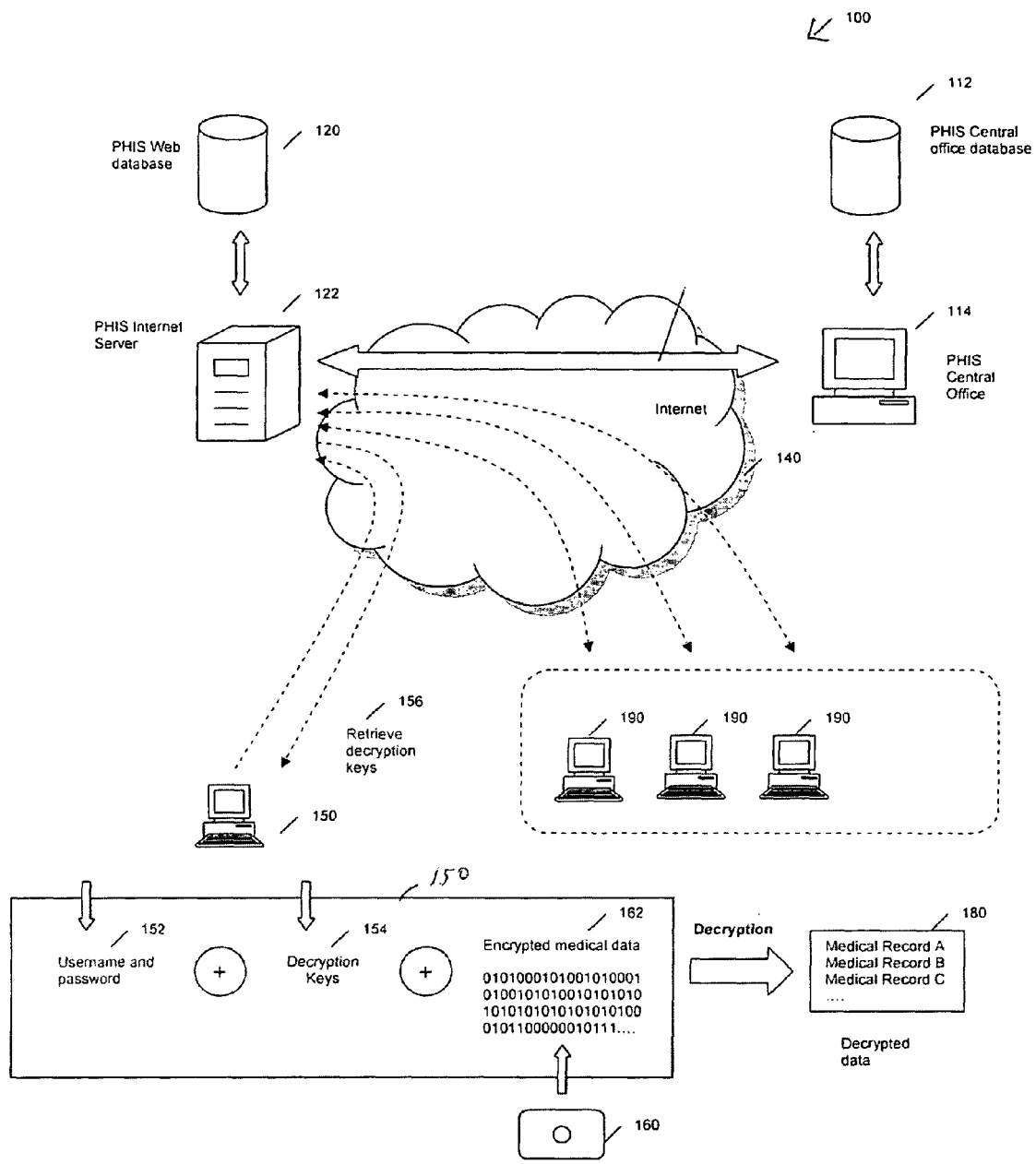
FIG. 1 illustrates a process for accessing personal medical according to one embodiment of the present invention.

Embodiments and methods of the present invention provide a way to make an individual's medical and surgical record secure, portable, easily accessible, and updateable. Authorized individuals are allowed to view an enrollee's vital statistics, medications, allergies, past medical history, past surgical history, physician/specialist name address and contact info, emergency contact information, date of birth, date of last update to medical record, health insurance, authentication code, health insurance information, address, personal phone numbers, emergency contacts, health care proxies, advance directives, family history, preventative maintenance procedures, labs, X-rays, stress test and list of available multimedia files in chronological order. These elements of records are merely illustrative examples. The medical records actually maintained according to the present invention may include other record elements or any combination of the above elements.

The embodiments provide the ability for an authorized physician to directly view actual copies of medical records from charts of various doctors, i.e., view patients blood labs, EKGs, Chest X-rays, CT scans, or MRI movies and angiograms/catheterizations, etc. The embodiments provide the ability for medical professionals to securely review all this information with a common computer setup or Internet connection.

Moreover, the PHIS system creates a document which includes a patient's full medical record (e.g. hospital visits, surgeries, doctors' visits of all specialties, etc.), unlike current Electronic Medical Record (EMR) systems that are only marketed to individual physicians or institutions. With current EMR systems only the individual medical professionals or institutions benefit from this digital organization. The patient is not provided with cohesive, continuous record that includes their encounters with various medical professionals. Patients generally see multiple specialists and/or visit multiple hospitals in their lifetime.

One embodiment provides a system that not only allows effective communication of medical history between patient and physician but among physicians themselves. This is done securely in compliance with HIPPA regulations even when physicians are in different institutions, offices, states, or countries. Other unique features include the security system. It requires the combination of the portable secure medium (or security key), password, and Web server's digital security key to open both tiers of information. These three types are referred to as the security triad. The present embodiment eliminates needless delays in ERs and doctors offices, allowing quick, informed, decisive actions to be taken during acute ER visits and chronic doctor office visits.

The present embodiment complies with HIPPA regulations, in that review of a patient's medical record requires consent from the patient. Verification is made so that sensitive documents are only reviewed by authorized health professionals in a secure manner. Updating the medical records is also secure and requires consent from both patient and physician as well according to one implementation.

The present embodiment provides a secure method to promptly access a patient's relevant medical records by treating physicians if the patient is unconscious. This is done by using a logo ID device. Such a device may be used as a portable secure medium. It can be inserted into an input slot of computers, Personal Digital Assistants, or other electronic devices.

One interesting feature of the present embodiment is the ability for users to keep portable, secure and medical records on their person at all times in the portable secure medium that can be updated as frequently as the users wish or as frequently as is mandated by their medical conditions. The medical records may be the complete records of the patient or only a relevant portion of the medical records, as determined by the patient's physician.

The records from various hospitals, physicians, and specialists an enrollee/patient that visited or seen can be stored in the secure medium and can be available to the patient and his or her physicians. Actual video, pictures and scans of the patient can be viewed directly by authorized health care professionals under a read-only mode. In addition, physicians with even the most basic computer skills and computer hardware would be able to access and view the medical records and information of a patient if so authorized.

If this portable record is lost or if the patient is unconscious, an automated process is used to ensure secure viewing of the medical records by an authorized physician. If the Internet access is not available, family members of the patient and health care proxies who have been previously selected by the patient may be easily notified. Such information is part of the information that is displayed automatically when the secure medium is inserted into a computer, i.e., without inputting the username and password, according to the present implementation.

People are enrolled to participate in the PHIS services described above. Potential enrollees undergo a consultation at home or in a central office. During this consultation the service will be explained to their satisfaction and forms will be signed contracting the service. An extensive medical history of the enrollee/patient is obtained, and the patient is then asked to sign release forms that will be sent to various institutions, physicians' offices, diagnostic facilities, etc. to collect the enrollee's medical records and information.

There are at least two tiers of security in the present embodiment. To view the first tier information, the username and password is required from the patient. The first tier information comprises a summary sheet. Thereafter, the second tier information may be obtained by an authorized physician by inputting the physician credentials (e.g., physician username and password). In the present embodiment, to access the second tier information the first tier information needs to be accessed first. In one implementation, the web server releases one of many multi-digit security keys to allow access to the second tier information. Once one of these web keys has been used, it is then blocked from future use. New Web server digital keys are created after every update.

If the Internet access is not available then conventional phone/fax is used to transmit the login ID and password. This process reduces the possibilities of security breaches, so that the enrollee's records cannot be accessed without his or her authorization. The security process, portability of medical records (e.g., complete records) for an enrollee, universal accessibility, updatability and HIPPA compliance are some of the useful features of the present embodiment.

In the present embodiment, once the portable secure medium is removed from the computer, all medical information of the patient is removed from the local computer. This is done by an executable program stored in the secure medium that is downloaded to the local computer when the access request is initiated or completed. This program is executed when the portable secure medium is removed from the computer. In other implementations, the executable program may be downloaded to the local computer by the Web server.

FIG. 1 illustrates a process 100 for accessing personal medical according to one embodiment of the present invention. A medical information management system includes a PHIS central office database 112, a PHIS central office computer 114, a PHIS Web database 120, and a PHIS Internet server 122. The computer 114 is provided at a secure site, so that only limited, authorized persons may have its access. The computer 114 is used to input personal medical information to the database 112. The computer 114 is also used to communicate with and transfer data to the server 122, so that the personal medical information stored in the database 112 can be copied to the Web database 120. Users and physicians can access the server 122 to obtain personal medical information from the Web database 120, e.g., using computers 150 and 190.

A user can access first tier information by inserting a portable secure medium 160 (e.g., MediDisk) into the computer 150. The portable secure medium can be of various different storage type and shape, e.g., have the shape of a credit card, necklace, or bracelet. The user inputs the username and password. As a result, the computer 122 accesses the server 122 to obtain a first decryption key 154. The decryption key is used to decrypt the encrypted medical data stored in the portable secure medium 160 to obtain medical information 180 (e.g., Records A, B, and C) that relates to the first tier information. In one implementation, the decryption key for the first tier information is stored within the portable secure medium, so that the personal medical information can be decrypted without accessing the server 122. In another implementation, the decryption key is obtained from the Web server upon entering proper username and password.

Figure 2:
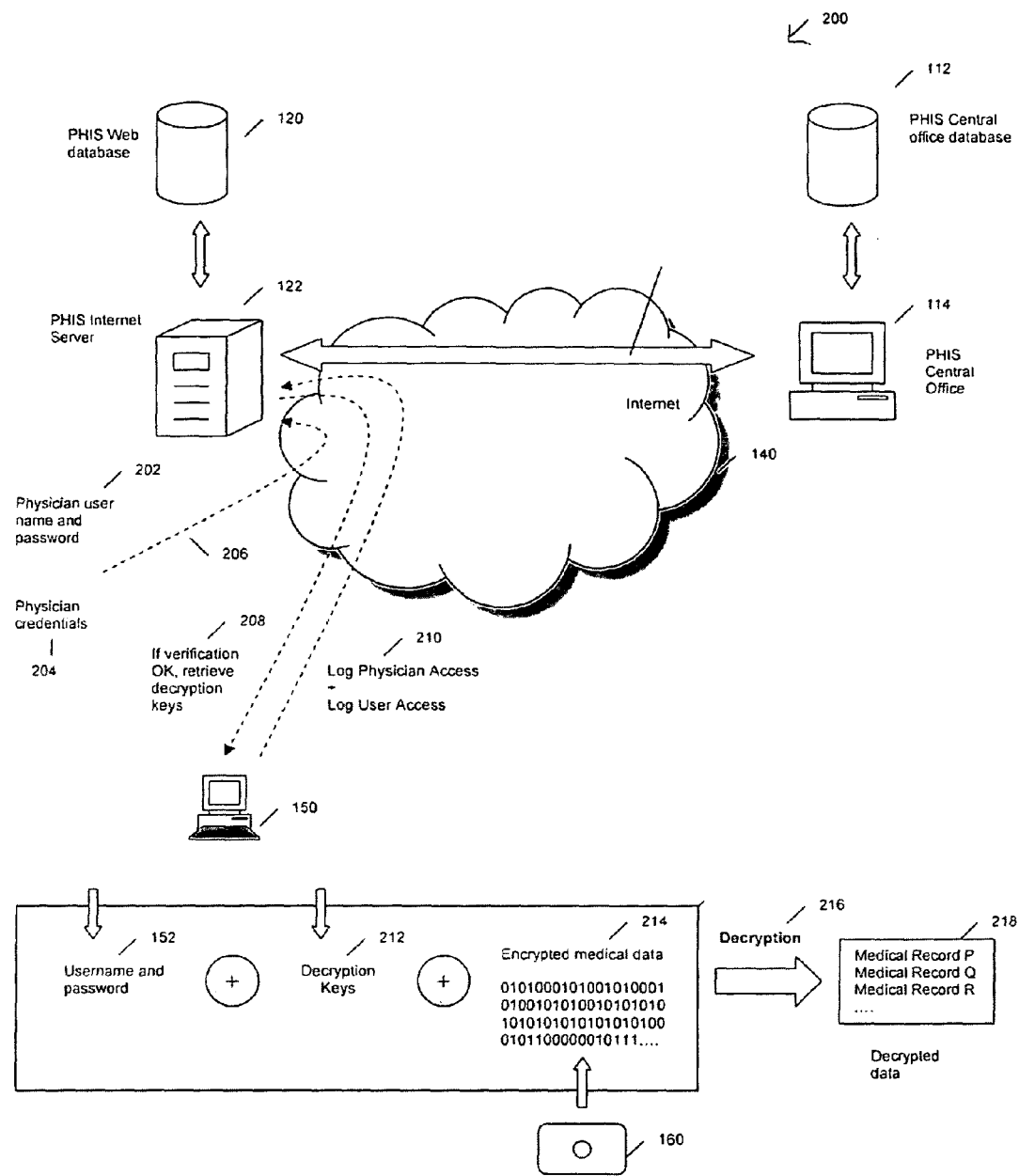
FIG. 2 illustrates a process for accessing personal medical information of second tier security according to one embodiment of the present invention.

FIG. 2 illustrates a process 200 for accessing personal medical information of second tier security according to one embodiment of the present invention. A physician inputs his/her username and password (numeral 202) and his/her credentials (numeral 204). These are sent to the server 122. Once the physician is authenticated, a second decryption key 212 is sent to the computer 150 to decrypt the medical information stored in the portable secure medium 160 to obtain medical information 218 (e.g., Records P, Q, and R) that relates to the second tier information. That is, the medical information 218 is obtained from the encrypted data 214 stored in the portable secure medium. Alternatively, the medical information related to the second tier information may be stored in the Web database 120 and is transmitted to the computer 150 with the second decrypted key upon verifying the physician information.

Figure 3:
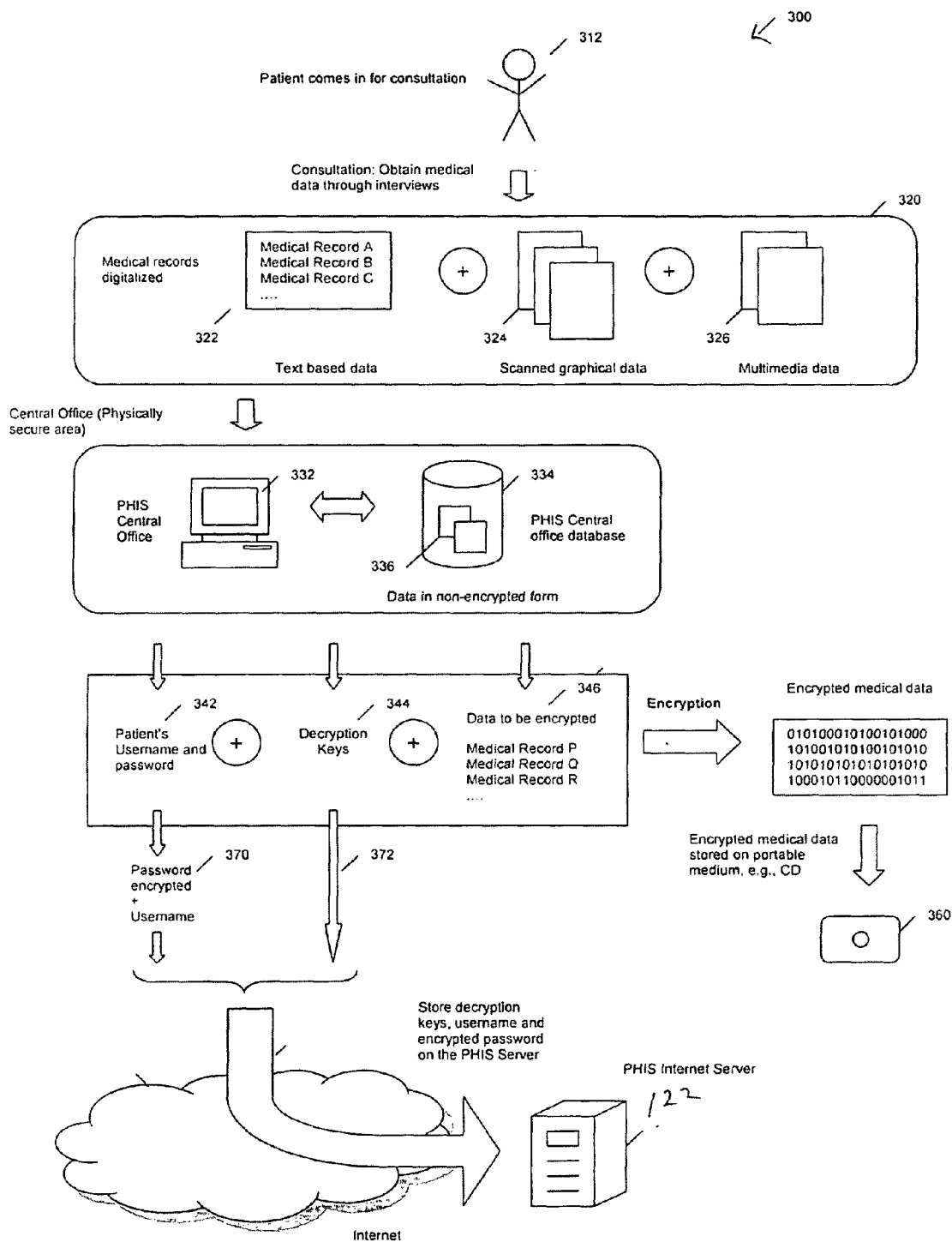
FIG. 3 illustrates a process for creating a portable secure medium and personal medical information for a given user according to one embodiment of the present invention.

FIG. 3 illustrates a process 300 for creating a portable secure medium 360 and personal medical information for a given user according to one embodiment of the present invention. At first, the user 312 comes in for consultation. The user's medical record 320 is obtained. The medical record includes text-based data 322, graphical data 324, multimedia data 326, and the like. These are scanned or otherwise converted to electronic form and sent to the central office 114. The central office is a tightly regulated environment to ensure the confidentiality and integrity of people's medical records. A computer 332 in the central office is used to store the user's medical record 320 into the database 334. In the present embodiment, the medical record is stored without being encrypted in the database 334 since it can only be accessed from a secure computer, i.e., computer 332. The computer 332 and the database 334 correspond to the computer 114 and the database 112 in FIG. 1.

The portable secure medium 360 is made at the central office using medical record 346. The medical record is associated with the username and password 342 and the decryption key 344. The medical record is encrypted and stored in the portable secure medium 360. The portable secure medium is then sent to the user to carry it with him/her for easy access when needed.

The medical record, the username, the password, and the decryption key are sent to the server 122, so that they can be stored in the Web database 120. These data are sent in encrypted form to prevent an unauthorized person from viewing while the data packets are being transferred.

Figure 4:
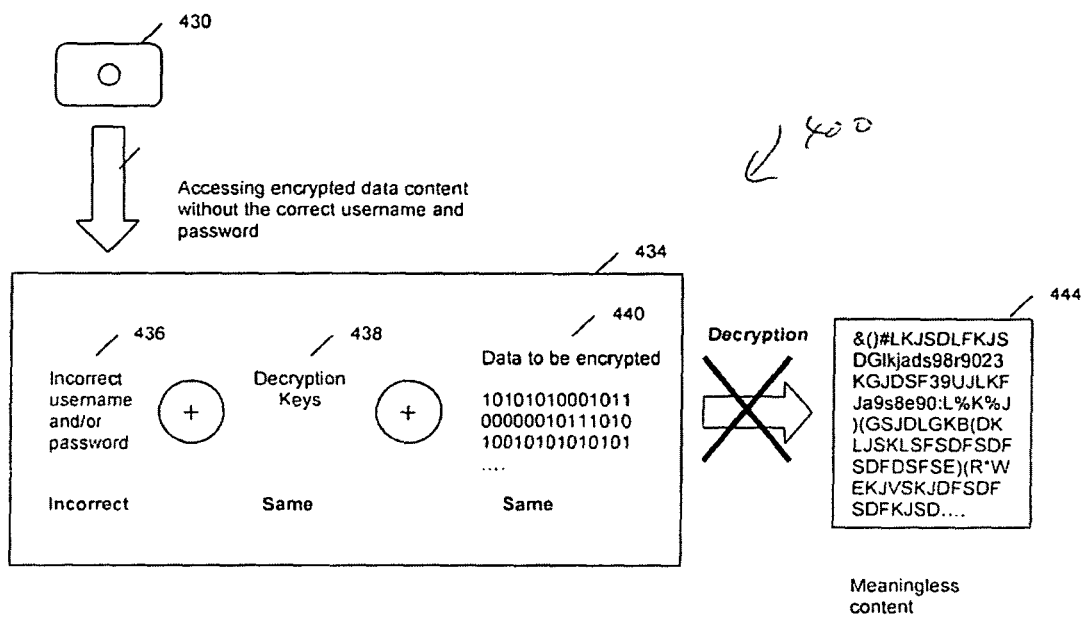
FIG. 4 illustrates a process where an incorrect username or password prevents access to the medical record stored in a portable secure medium according to one embodiment of the present invention.

FIG. 4 illustrates a process 400 where an incorrect username or password prevents access to the medical record stored in a portable secure medium 430 according to one embodiment of the present invention. The portable secure medium 430 includes encrypted data 440 and a decryption key 438. Meaningless content 444 is output if an incorrect username or password (numeral 436) is input. In one implementation, the decryption key may be stored at the server side and received from the server when the username and password are entered. If an incorrect username and/or password are entered, the decryption key is not transmitted to the client computer, which prevents the medical information stored in the secure medium from being accessed.

Figure 5:
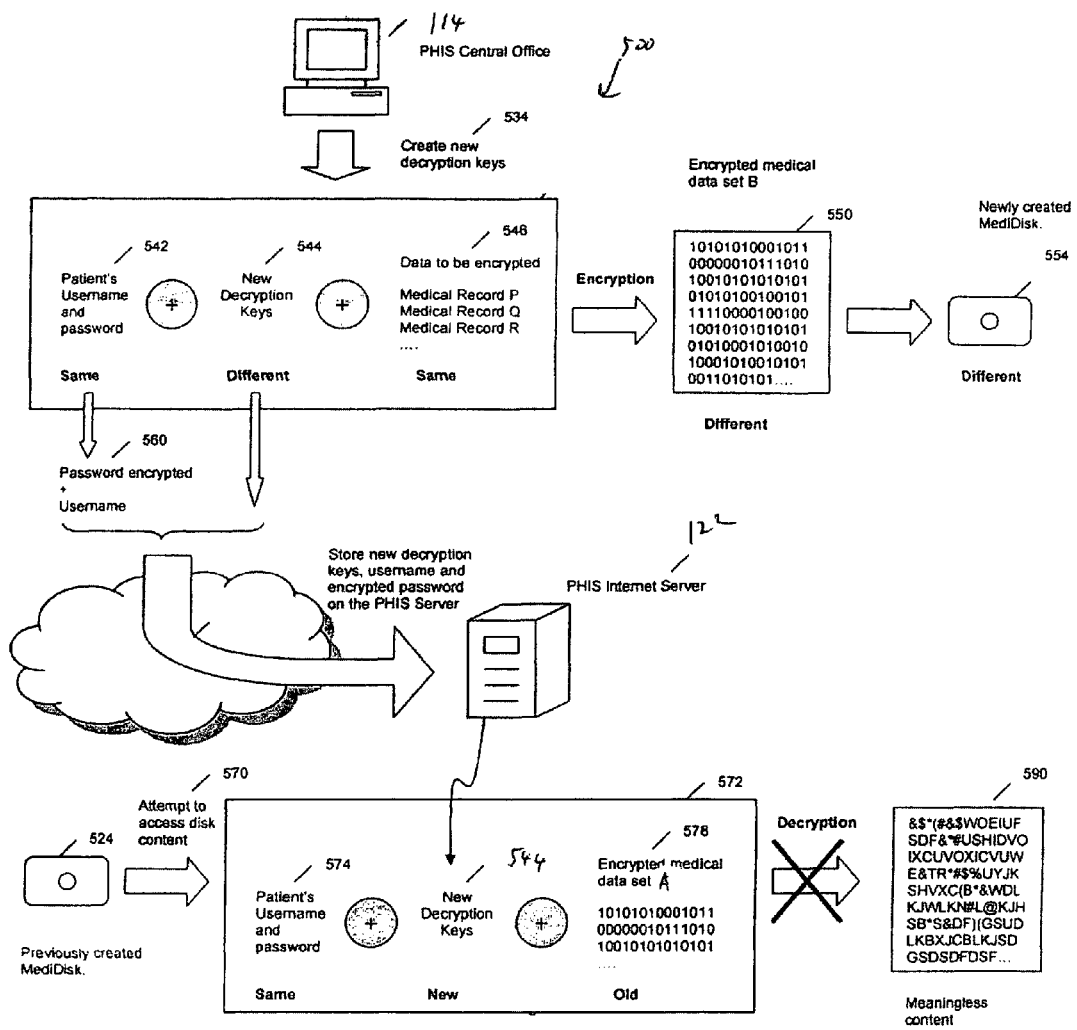
FIG. 5 illustrates a process for creating a new portable secure medium when the previously created portable secure medium is lost or stolen, according to one embodiment of the present invention.

FIG. 5 illustrates a process 500 for creating a new portable secure medium when the previously created portable secure medium is lost or stolen, according to one embodiment of the present invention. A new portable secure medium 554 is created by the central office 114. The same username and password and a new decryption key 544 are associated with the medical records 546 of the user. The resulting encrypted data 550 is stored in the new portable secure medium 554 and sent to the user. The username and password are encrypted (numeral 560) and sent to the server 122 to be stored. The decryption key is also sent to the server 122 with the username and password in the present implementation.

In the present embodiment, the decryption key is stored in the server 122 and sent to a client computer upon a request. Accordingly, in the present embodiment, once the username and password have been associated with the new decryption key 544, it is not possible to access the medical record stored in the previous portable secure medium 524. For example, even if the correct username and password are inputted, the server sends the new decryption key 544. The new decryption key is applied to the medical data 578 that have been encrypted using a different key (i.e., the medical data 578 is different from the medical data 550) so that a meaningless content is output.

Figure 6:
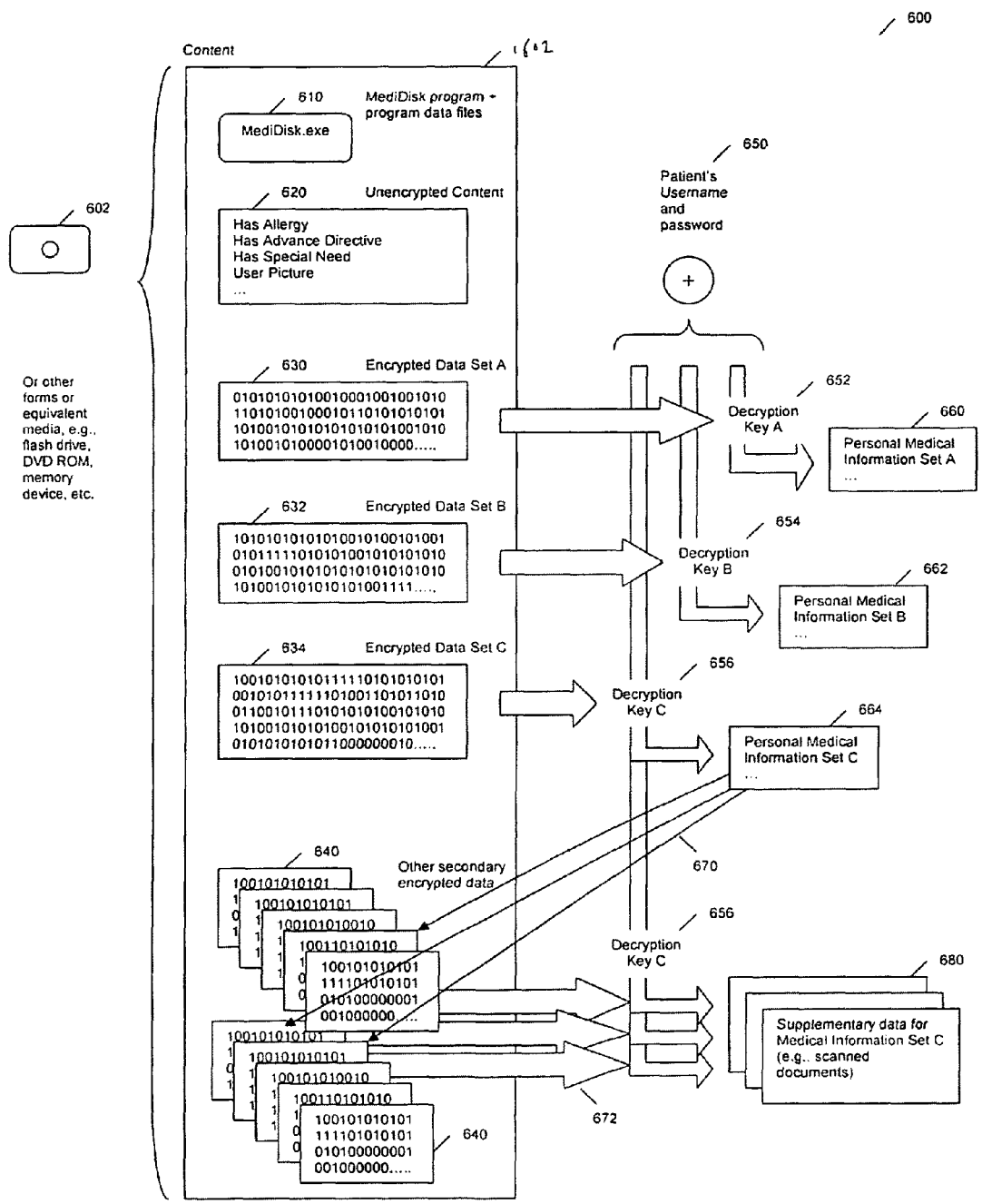
FIG. 6 illustrates contents provided within a portable secure medium according to one embodiment of the present invention.

FIG. 6 illustrates contents provided within a portable secure medium 602 according to one embodiment of the present invention. The portable secure medium 602 includes one or more executable files 610, an unencrypted content 620, a first encrypted data set 630, a second encrypted data set 632, a third encrypted data set 634, and one or more secondary data sets 640. The first encrypted data set is associated with a first decryption key 652, so that first medical information 660 can be obtained from the first encrypted data set using the first decryption key and the username and password 650. The second encrypted data set 632 is associated with a second decryption key 654, so that second medical information 662 can be obtained from the second encrypted data set using the second decryption key the username and password 650. The third encryption data set is associated with a third decryption key 656, so that third medical information 664 can be obtained from the third encrypted data set using the third decryption key the username and password 650. In the present implementation, the secondary data sets 640 are associated with the third decryption key, so that supplementary data, e.g., scanned documents, can be obtained using the third decryption key and the username and password. In other implementations, the secondary data set may be associated with other keys.

Figure 7A:
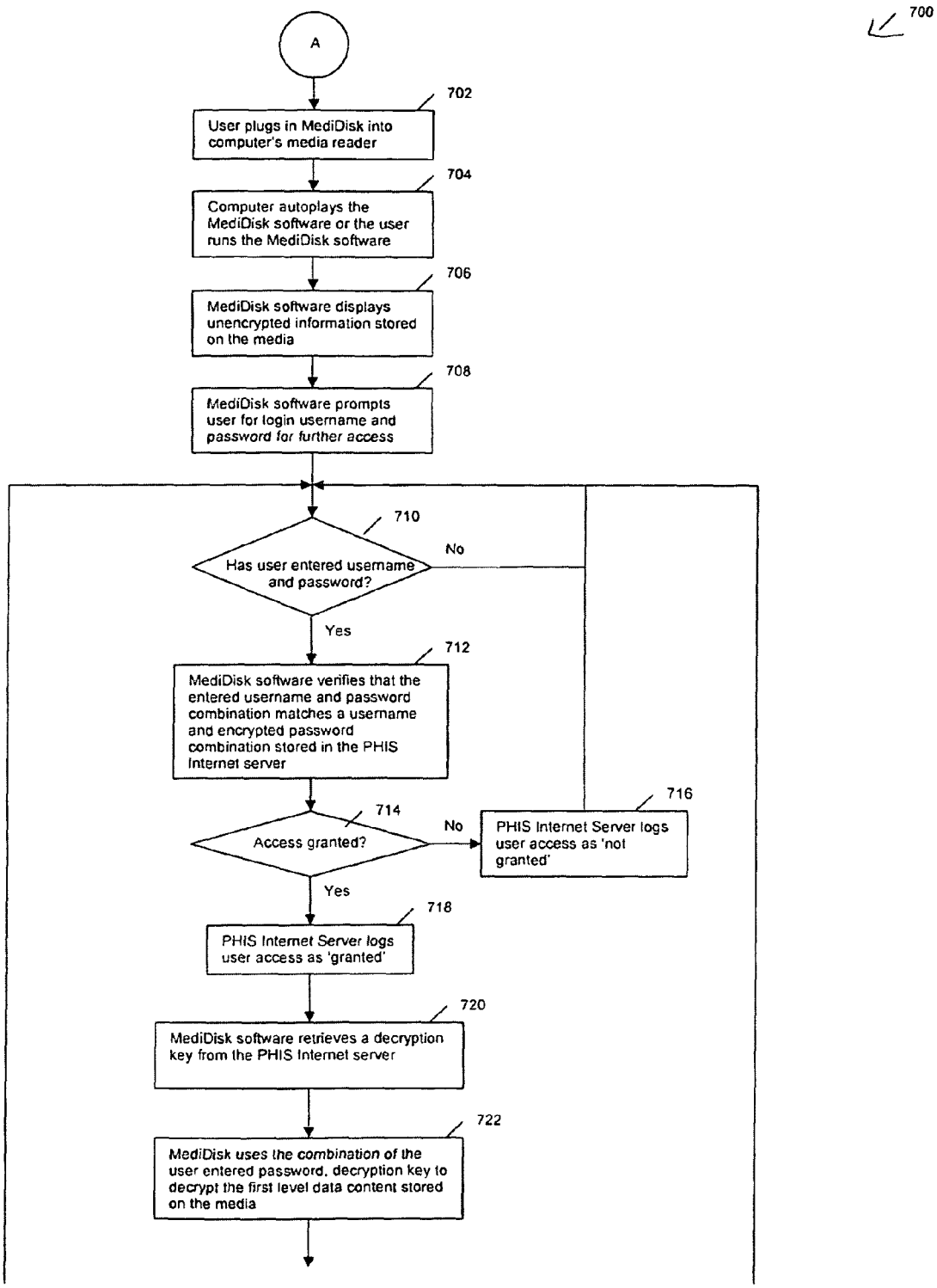
FIGS. 7A-7C illustrate a process on the workings of PHIS according to one embodiment of the present invention.
Figure 7B:
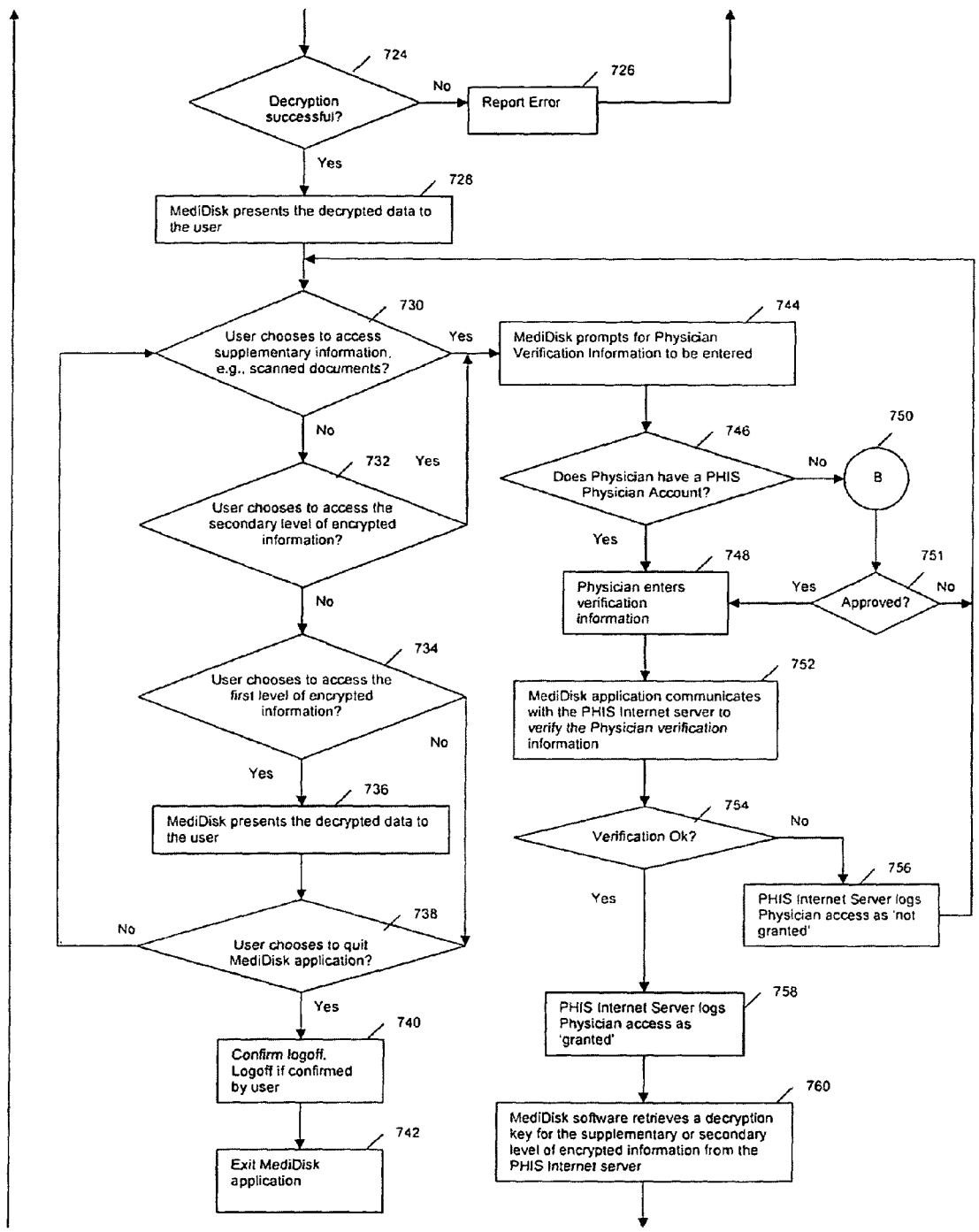
Figure 7C:
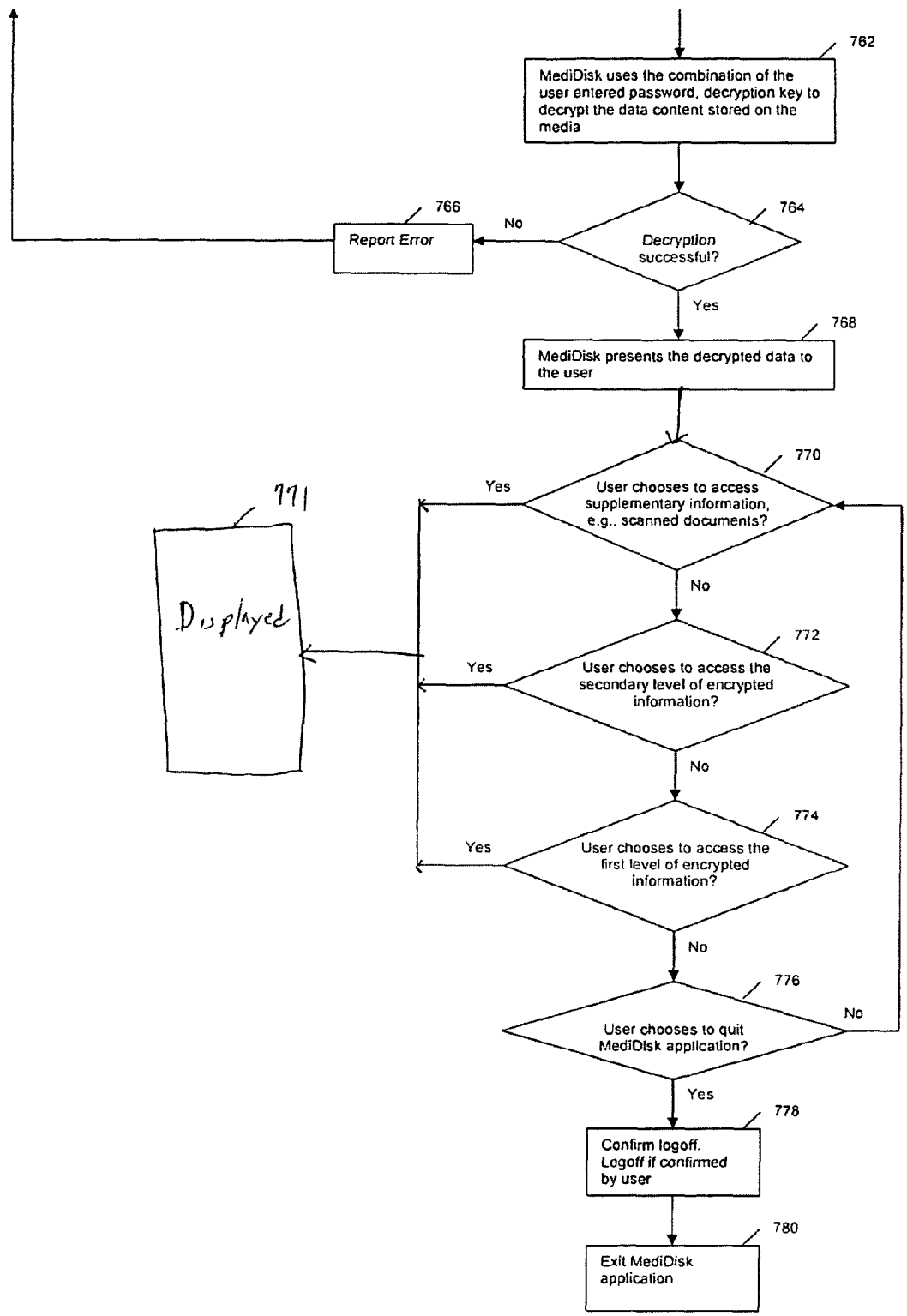

FIGS. 7A-7C illustrate a process 700 on the workings of PHIS according to one embodiment of the present invention. At step 702, the user inserts the portable secure medium into a computer. The computer executes the secure medium software stored in the portable secure medium (step 704). Alternatively, the user may run the software manually. At first, the software displays unencrypted information stored in the portable secure medium. Such information is generally non-sensitive information, e.g., the name of the patient and his/her doctor. For further information, the username and the password are prompted (step 708). Once the username and password are inputted (step 710), these are checked with the username and password stored in the server 122 (step 712). In the present implementation, the password is stored in the server in encrypted form. If the username and password are verified, then the access to the portable secure medium is granted and the server logs the user access as being "granted" (steps 714 and 718). Otherwise, the server logs the user access as being "not granted" (step 716). A first decryption key is retrieved from the server (step 722). The first decryption key is used to decrypt the content in the portable secure medium. If successful, the decrypted data are displayed to the user (steps 724 and 728). Otherwise, an error is reported (step 726).

The user may choose to access supplementary information. If so, physician verification information is prompted (step 744). Otherwise, it is determined whether or not the user wishes to access the second tier information (step 732). If so, the physical verification information is prompted (step 744). If not, it is determined whether or not the user wishes to access the first tier information (step 734). If so, the first tier information is displayed to the user. If not, it is determined whether or not the user wishes to quit the application. If so, the application is terminated and the portable secure medium is removed from the computer (steps 740 and 742). If not, the process returns to step 730.

Referring back to step 744, the process determines whether or not the physician has a PHIS physician account (step 746). If so, the physician enters the verification information (step 748). The inputted verification information is checked with the information stored in the server 122 (step 752). If verification is confirmed, the server logs the physician access as being "granted" (steps 754 and 758). A second decryption key is retrieved from the server to decrypt the second tier information stored in the portable secure medium (steps 760 and 762). The secondary tier information includes the supplementary information. If the decryption is successful, the decrypted data are ready for viewing by the user (step 768). If the user chooses to access the supplementary information, it is displayed (steps 770 and 771). If the user chooses to access the second tier information, it is displayed (steps 771 an 772). If the user chooses to accesses the first tier information, it is displayed (steps 771 and 774). It determined whether or not the user wishes to quit the application (step 776). If so, the application is terminated and the portable secure medium is removed from the computer (step 778 and 780). Otherwise, the process returns to step 770.

Figure 8:
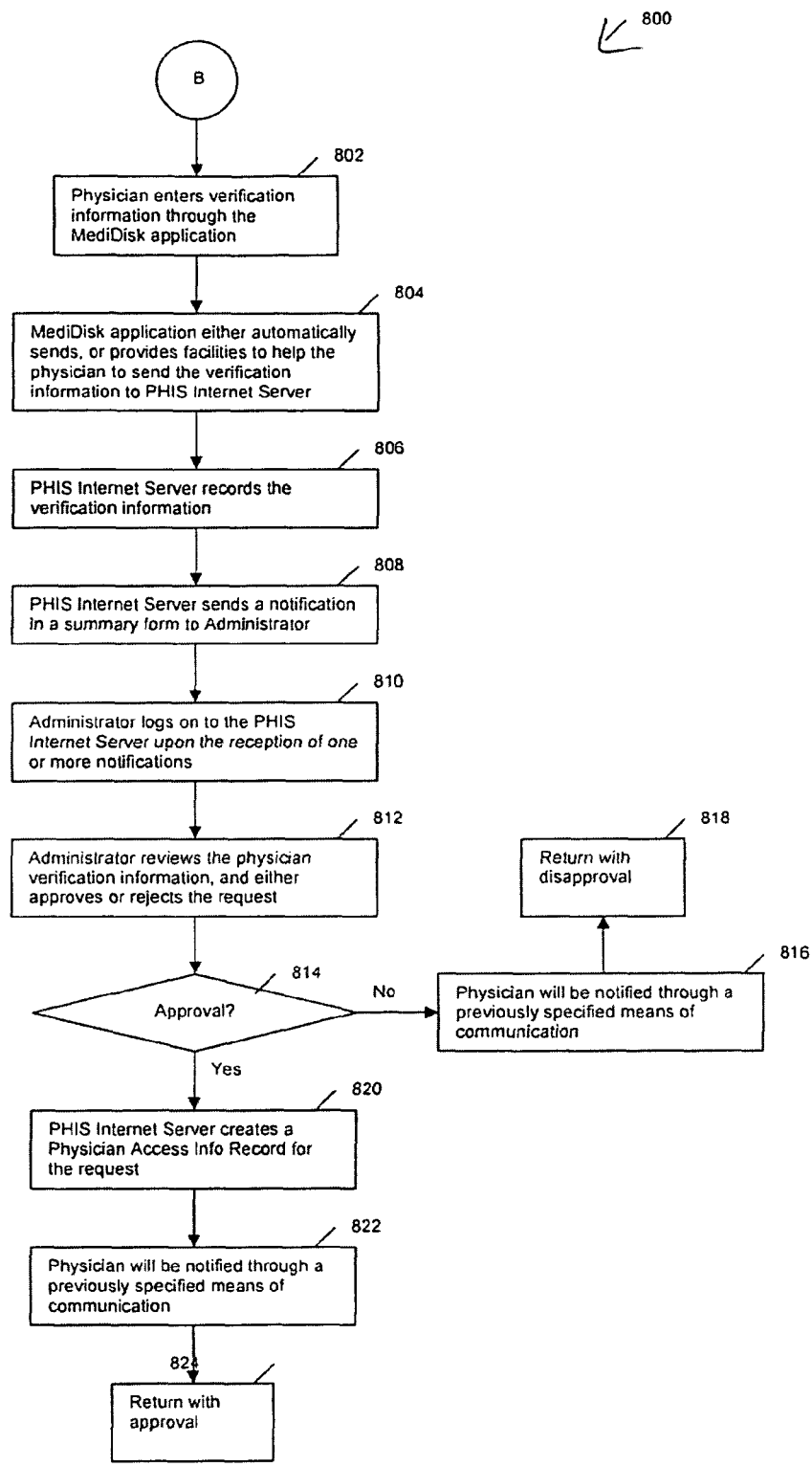
FIG. 8 illustrates a process for creating a physician verification information record on the server according to one embodiment of the present invention.

FIG. 8 illustrates a process 800 for creating a physician verification information record on the server 122 according to one embodiment of the present invention. The process 800 corresponds to the step 750 in FIG. 7B. At step 802, a physician enters verification information on the client computer. The inputted verification information is sent to the Internet server 122 (step 804). The verification information may be sent automatically by the portable secure medium software or by other means. The server 122 records the verification information (step 806). The server sends a notification to an administrator in the central office (step 808). The administrator logs onto the server 122 and review the physician verification information (steps 810 and 812). The request is approved or rejected by the administrator upon review of the physician verification information. It is determined whether or not the administrator has approved the request (step 814). If so, the server 122 creates a physician access information record for the request (step 820). The physician is notified through a previously specified means of communication (steps 822 and 824). If not approved, the physician is also notified of the disapproval (steps 816 and 818).

Figure 9A:
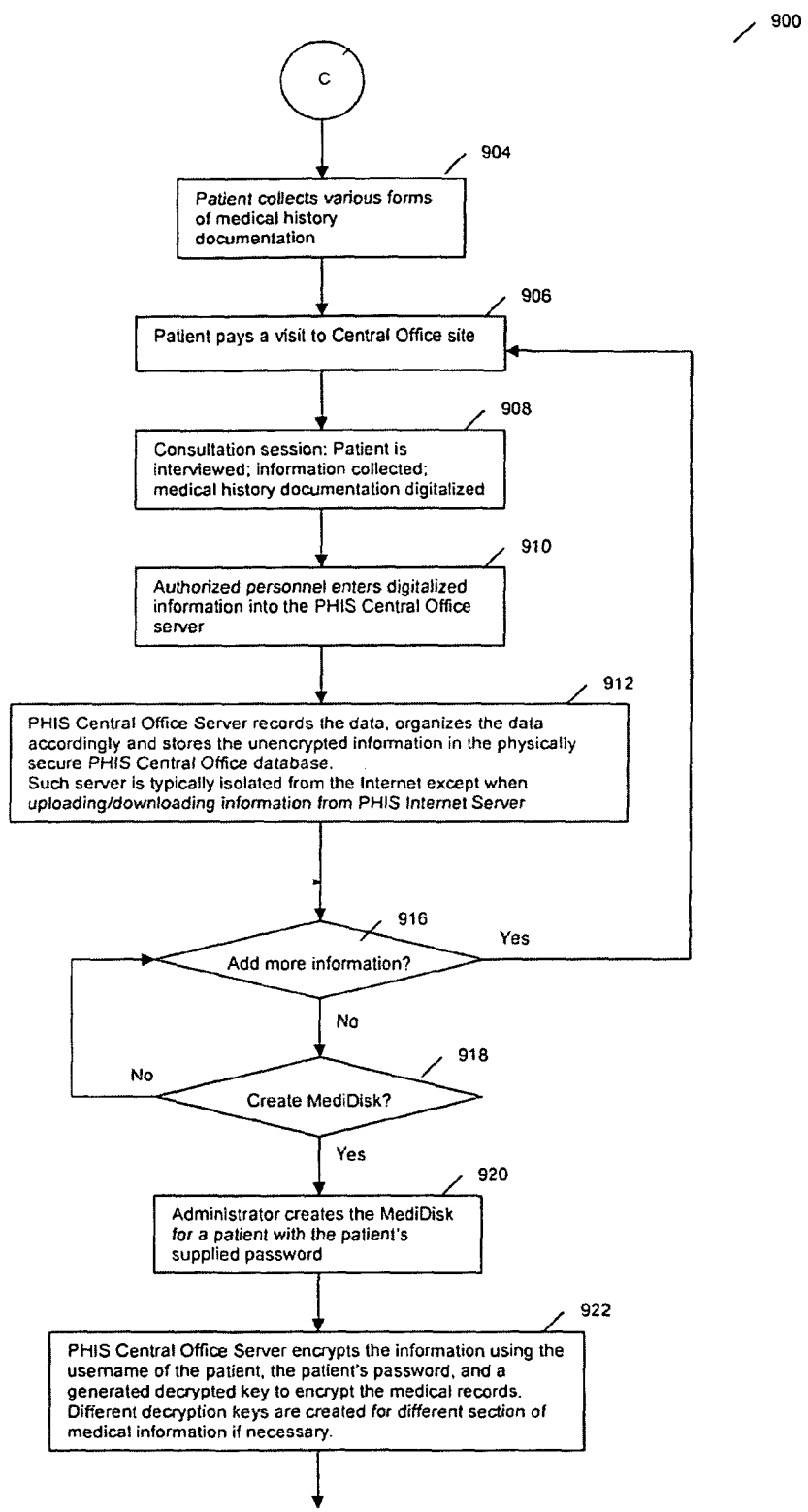
FIGS. 9A-9B illustrate a process for preparing a portable secure medium according to one embodiment of the present invention.
Figure 9B:
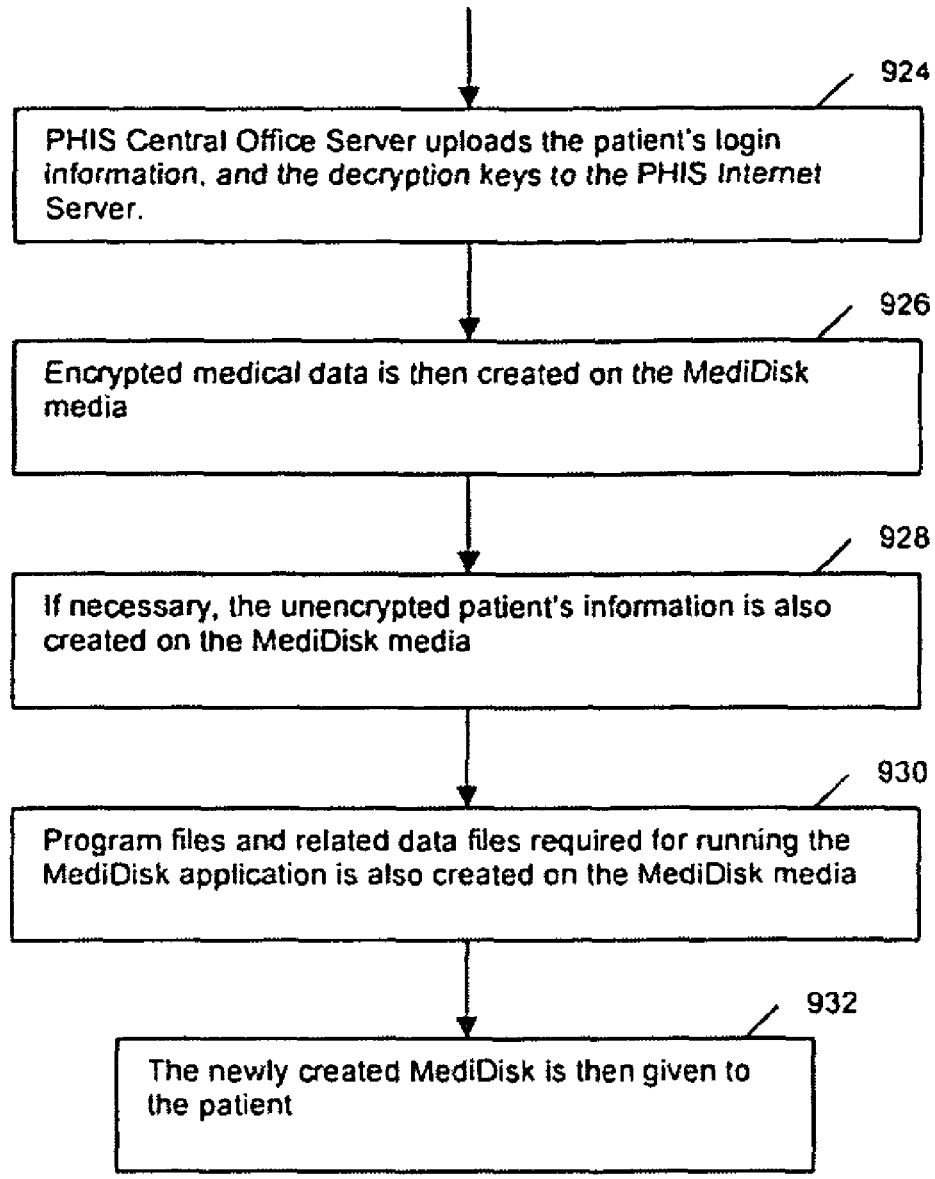

FIGS. 9A-9B illustrate a process 900 for preparing a portable secure medium according to one embodiment of the present invention. At step 904, a patient collects various forms of medical history documentation. The patient visits the central office (step 906). A consultation with the patient is conducted (step 908). The patient is interviewed, and relevant medical records of the patient are collected and converted into electronic form. An authorized person at the central office stores the converted medical records into the central office server 114 (step 910). The records are organized and stored within the central office database 112 (step 912). The database 112 is configured to be only accessed using the central office sever 114 for security reasons. Additional medical records are added if necessary (step 916). If there are no more records to be added, it is determined whether or not a portable secure medium is to be created (step 918). If so, the administrator creates the portable secure medium for the patient (step 920). The central office server 114 encrypts the medical records using the username and password of the patient (step 922). A decryption key is generated at this time. If necessary, different decryption keys are created for different sections of the medical records. The central office server 112 uploads the patient's login information and the decryption keys to the Internet server 122 (step 924). Encrypted medical data are stored in the portable secure medium (step 926). If necessary, unencrypted patient's information is also stored in the portable secure medium (step 928). The patient may or may not wish to include such information in his/her portable secure medium according to preference. Program files and other related data files that are needed to run the portable secure medium application are also stored in the portable secure medium (step 930). The newly created portable secure medium is given to the patient (step 932).

The present invention has been described in terms of specific embodiments. These embodiments have been provided for illustrative purposes and are not to be used to limit the scope of the present invention. As those skilled in the art will understand, one or more features of the above embodiments may be changed, modified, or altered without departing from the scope of the present invention.

What is claimed is:

1. A computer implemented method for managing a person's medical information, the method comprising:
    receiving a first request to access a first tier of medical information of a given person, the request including first security information associated with a portable secure medium associated with the given person;
    enabling access to the first tier information associated with the medical information of the given person upon authenticating the first request;
    receiving a second request to access a second tier of the medical information of the given person responsive to enabling access to the first tier information, the second request including second security information associated with a medical professional; and
    enabling access to the second tier information associated with the medical information of the given person upon authenticating the second request.

2. The method of claim 1, wherein the second request is authenticated only if the first request has been authenticated.

3. The method of claim 1, further comprising authenticating the first and second requests responsive in part to the portable secure medium associated with the given person being connected to a processing device, the processing device being used as a client to communicate with a server.

4. The method of claim 1, wherein the enabling access to the second tier information includes receiving the second tier information stored in a server at a client to which the portable secure medium associated with the given person is coupled.

5. The method of claim 1, wherein the enabling access to the second tier information further includes receiving a decryption key at a client from a server to access the second tier information, the second tier information being received by the client in encrypted form.

6. The method of claim 1, further comprising:
receiving a first decryption key at a client at which the first request has been received once the first request has been authenticated; and
receiving a second decryption key at the client in response to the second request once the second request has been authenticated.

7. The method of claim 1, wherein the first request is received by a client to which the portable secure medium associated with the given person is coupled, the client being used to communicate with a remotely located server, and wherein the first tier information is stored in the portable secure medium in encrypted form.

8. The method of claim 1, wherein the second tier information is stored in a server and received by a client after the second request has been authenticated, the second tier information being received by the client in encrypted form.

9. The method of claim 1, wherein the first request is received after the portable secure medium associated with the given person has been coupled to a client configured to communicate with a server that is provided at a remote location from the client.

10. The method of claim 9, wherein the portable secure medium serves as a security key that enables the first request to be processed by the server.

11. The method of claim 1, further comprising:
enabling display of non-confidential information about the given person without requiring security information input.

12. The method of claim 11, wherein the enabling display is performed after the portable secure medium is coupled to a processing device.

13. A server comprising:
a network interface to communicate with clients;
a storage device to store medical information of users; and
a computer readable medium including code for receiving a first request to access a first tier of medical information of a given user, the request including first security information associated with a portable secure medium associated with the given user;
code for providing access to the first tier information associated with the medical information of the given user upon authenticating the first request;
code for receiving a second request to access a second tier of the medical information of the given user responsive to providing access to the first tier information, the second request including second security information associated with a medical professional; and
code for providing access to the second tier of information associated with the medical information of the given user upon authenticating the second request.

14. One or more computer-readable storage media embodying computer-readable instructions that, in response to execution by a computing device, cause the computing device to perform operations comprising:
receiving a first request to access a first tier of medical information of a given person, the request including first security information associated with a portable secure medium associated with the given person;
enabling access to the first tier information associated with the medical information of the given person upon authenticating the first request;
receiving a second request to access a second tier of the medical information of the given person responsive to enabling access to the first tier information, the second request including second security information associated with a medical professional; and
enabling access to the second tier information associated with the medical information of the given person upon authenticating the second request.

15. The one or more computer-readable storage media of claim 14, wherein the second request is authenticated only if the first request has been authenticated.

16. The one or more computer-readable storage media of claim 14, wherein the operations further comprise authenticating the first and second requests responsive in part to the portable secure medium associated with the given person being connected to a processing device, the processing device being used as a client to communicate with a server.

17. The one or more computer-readable storage media of claim 14, wherein the operations further comprise enabling access to the second tier information by receiving the second tier information stored in a server at a client to which the portable secure medium associated with the given person is coupled.

18. The one or more computer-readable storage media of claim 14, wherein the operations further comprise enabling access to the second tier information by receiving a decryption key at a client from a server to access the second tier information, the second tier information being received by the client in encrypted form.

19. The one or more computer-readable storage media of claim 14, wherein the operations further comprise:
receiving a first decryption key at a client at which the first request has been received once the first request has been authenticated; and
receiving a second decryption key at the client in response to the second request once the second request has been authenticated.

20. The one or more computer-readable storage media of claim 14, wherein the first request is received by a client to which the portable secure medium associated with the given person is coupled, the client being used to communicate with a remotely located server, and wherein the first tier information is stored in the portable secure medium in encrypted form.

21. The one or more computer-readable storage media of claim 14, wherein the second tier information is stored in a server and received by a client after the second request has been authenticated, the second tier information being received by the client in encrypted form.

22. The one or more computer-readable storage media of claim 14, wherein the first request is received after the portable secure medium associated with the given person has been coupled to a client to communicate with a server that is provided at a remote location from the client.

23. The one or more computer-readable storage media of claim 22, wherein the portable secure medium serves as a security key that enables the first request to be processed by the server.

24. The one or more computer-readable storage media of claim 14, wherein the operations further comprise:
   enabling display of non-confidential information about the given person without requiring security information input.

25. The one or more computer-readable storage media of claim 24, wherein the operations further comprise enabling display of the non-confidential information after the portable secure medium is coupled to a processing device.

26. A system comprising:
   means for receiving a first request to access a first tier of medical information of a given person, the request including first security information associated with a portable secure medium associated with the given person;
   means for enabling access to the first tier information associated with the medical information of the given person upon authenticating the first request;
   means for receiving a second request to access a second tier of the medical information of the given person responsive to enabling access to the first tier information, the second request including second security information associated with a medical professional; and
   means for enabling access to the second tier information associated with the medical information of the given person upon authenticating the second request.

27. The system of claim 26, wherein the means for receiving the first request comprises means for receiving the first request after the portable secure medium associated with the given person has been coupled to a client configured to communicate with a server that is provided at a remote location from the client.

28. The system of claim 26, further comprising:
   means for receiving a first decryption key at a client at which the first request has been received once the first request has been authenticated; and
   means for receiving a second decryption key at the client in response to the second request once the second request has been authenticated.

* * * * *